United States Patent
Guerret et al.

(10) Patent No.: US 8,354,466 B2
(45) Date of Patent: *Jan. 15, 2013

(54) METHOD FOR FORMULATING AGROCHEMICAL ACTIVE INGREDIENTS SO AS TO REGULATE THEIR RELEASE KINETICS, PROTECT THEM FROM OUTSIDE STRESSES, AND KEEP THEIR USERS SAFE

(75) Inventors: Olivier Guerret, La Tour de Salvagny (FR); Jean-Marc Suau, Lucenay (FR); Yves Kensicher, Theize (FR)

(73) Assignee: Coatex S.A.S., Genay (FR)

( * ) Notice: Subject to any disclaimer, the term of this patent is extended or adjusted under 35 U.S.C. 154(b) by 277 days.

This patent is subject to a terminal disclaimer.

(21) Appl. No.: 12/668,662

(22) PCT Filed: Jun. 13, 2008

(86) PCT No.: PCT/IB2008/001564
§ 371 (c)(1),
(2), (4) Date: Jan. 12, 2010

(87) PCT Pub. No.: WO2009/007810
PCT Pub. Date: Jan. 15, 2009

(65) Prior Publication Data
US 2010/0203170 A1 Aug. 12, 2010

(30) Foreign Application Priority Data
Jul. 12, 2007 (FR) .................................. 07 05045

(51) Int. Cl.
*C08G 18/42* (2006.01)
*A01N 25/00* (2006.01)
*A01N 25/08* (2006.01)
*A61K 9/00* (2006.01)

(52) U.S. Cl. ........ 524/500; 424/400; 424/405; 424/409; 514/937

(58) Field of Classification Search .................. 514/937; 424/400, 405, 409; 524/500
See application file for complete search history.

(56) References Cited

U.S. PATENT DOCUMENTS

| | | | |
|---|---|---|---|
| 5,292,843 A | 3/1994 | Jenkins et al. | |
| 5,342,883 A | 8/1994 | Jenkins et al. | |
| 5,629,261 A * | 5/1997 | Narayanan et al. | 504/361 |
| 5,916,967 A | 6/1999 | Jones et al. | |
| 6,372,259 B1 * | 4/2002 | Kumar | 424/497 |
| 6,746,635 B2 * | 6/2004 | Mathiowitz et al. | 264/4.3 |
| 2006/0159758 A1 * | 7/2006 | Gandhi et al. | 424/472 |
| 2010/0113617 A1 * | 5/2010 | Guerret et al. | 514/772.6 |
| 2010/0152094 A1 * | 6/2010 | Guerret et al. | 512/2 |

FOREIGN PATENT DOCUMENTS

| | | |
|---|---|---|
| EP | 0 875 557 | 11/1998 |
| EP | 1 655 351 | 5/2006 |
| JP | 2005 298474 | 10/2005 |
| WO | 99 65958 | 12/1999 |

* cited by examiner

*Primary Examiner* — Abigail Fisher
(74) *Attorney, Agent, or Firm* — Oblon, Spivak, McClelland, Maier & Neustadt, L.L.P.

(57) ABSTRACT

The invention pertains to a new method for formulating any agrochemical active ingredient so as to protect the user, protect this active ingredient from outside stresses, and control its release kinetics. It relies on the use of acrylic and thickening emulsions with a pH greater than five and containing hydrophobic groups in order to trap said active ingredient. The invention also pertains to the various embodiments of the active ingredient thereby formulated: a mixture in water of that active ingredient with these thickening emotions, a dispersion of solid particles of these polymers and this active ingredient after a certification, and the solid particles obtained in a dried state after the water has been removed. Finally, the invention pertains to the use of these various formulations in order to protect and active ingredient, protect its user, and slow its release kinetics.

18 Claims, No Drawings

METHOD FOR FORMULATING AGROCHEMICAL ACTIVE INGREDIENTS SO AS TO REGULATE THEIR RELEASE KINETICS, PROTECT THEM FROM OUTSIDE STRESSES, AND KEEP THEIR USERS SAFE

This application is a 371 of PCT/IB08/01564 filed June 13, 2008.

SUMMARY OF THE INVENTION

The invention pertains to a new method for formulating agrochemical active ingredients in order to keep the people who handle them safe, protect these ingredients from outside stresses, and regulate their release kinetics. It also offers the ability to formulate these active ingredients in two delivery methods which are particularly interesting for the person skilled in the art: that of a sprayable liquid (aqueous dispersion or solution) or a spreadable (granulated) solid. It also makes it possible to meet all of the aforementioned requirements, regardless of what the agrochemical active ingredient in question is: This means it is a "universal" method.

The invention relies upon the use of acrylic and water-soluble emulsions with a pH greater than 5, containing hydrophobic groups. These emulsions make it possible to trap the agrochemical active ingredients by encapsulation, in order to encourage their protection from the environment. Thereby formulated, the active ingredient will not only be protected from outside stresses, but the user too will be protected from the possible harmful effects of said active ingredient. Additionally, the active ingredient thereby trapped will have extended action, because it will be released over longer periods of time.

Furthermore, the invention makes it possible to formulate active ingredients via the 2 "conventional" methods used by the end-user: in the form of a liquid which is sprayed, or in the form of a solid which is intended to be spread, with both of these forms also being directly injectable into the soil. Finally, the library of hydrophobic groups made available to the manufacturer is so thorough that the person skilled in the art will be capable of encapsulating any agrochemical active ingredient by wisely choosing the hydrophobic group present in the inventive acrylic emulsion.

BACKGROUND DEFINITIONS

Agrochemical active ingredient: in the context of this invention, this expression refers to any substance with an activity on soil, fauna, or flora, which could refer to (without being limited thereto) a molecule with a herbicidal, pesticidal, or fungicidal effect, a fertilizer, or a defoliant. For the sake of better comprehension, the Application may use the shortened expression "active ingredient", in order to designate the "agrochemical active ingredient".

HASE: acronym for Hydrophobically Alkali Swellable Emulsion. This term refers to acrylic thickeners based on a (meth)acrylic acids, an ester of these acids, and a monomer comprising at least one hydrophobic unit.

TECHNICAL PROBLEM AND PRIOR ART

Protecting the agrochemical active ingredients, both in the initial formula that contains them (like a fertilizer, pesticide, herbicide, etc.) and in the surfaces onto which they are to be applied (like the ground, a tree, a plant, etc.) is a major challenge for the person skilled in the art.

The active ingredients must first be protected within the formula that they are part of. This is because these inactive ingredients may prove to be chemically unstable and vulnerable to outside stresses such as oxidations, as indicated in the document "Dégradation catalytique de carbamates herbicides déposés sur bentonites homoïoniques—IV—Cas du carbetamide" (Weed Research 26 (5), October 1986, pp. 315-324). Additionally, certain active ingredients are dangerous for users: for example, EPTC (ethyl di-N-propylthiocarbamate), a molecule with an herbicidal activity, emits toxic nitrogen oxide- and sulfur oxide-based gases as it decomposes, and is considered to be toxic when it is absorbed through the skin, inhaled, or digested.

These active ingredients must also have an extended action over time, in order to prevent overdosing them in the formulas (which increases the risk of user exposure) and/or increasing the number of spreading or spraying actions (which are time- and equipment-hungry). Additionally, the person skilled in the art ordinarily tends to overdose the active ingredient, in order to compensate for inevitable losses related to the degradation of that ingredient. Protecting an agrochemical active ingredient, with the intent of extending its effectiveness over time, makes it possible to reduce the quantity of said ingredient being used, which constitutes a major challenge for the person skilled in the art.

It is also necessary to offer a technique for formulating the active ingredients, in both a liquid and solid state, because these are the two forms preferred by the end user. Maintaining this degree of flexibility when choosing the technique for implementing the product (spraying, spreading, or injecting into the ground) is therefore an integral part of the Applicant's requirements.

Finally, providing a method that makes it possible to protect an agrochemical active ingredient, regardless of the molecule, would constitute a degree of technical progress, as a person skilled in the art is often confronted with molecules of different natures and structures. To demonstrate this, it is sufficient to examine the number and diversity of molecules with activity in the field of herbicides alone, which include:
- mineral herbicides (such as calcium cyanamide, iron sulfate and sodium chlorate);
- organic herbicides:
  - that act by root penetration (dinitroanilines, urea substitutes, triazines),
  - that act by leaf penetration (synthetic phytohormones, nitro colorants derived from phenol and dinitrophenol, carbamates, pyrilide-based quaternary ammonias and products in the family of glyphosates such as Roundup™),
  - that act by both root and leaf penetration (imidazolinones, dyphenyl-ethers).

Therefore, encapsulating agrochemical active ingredients has been sought for years, in order to meet all of the aforementioned restrictions. To date, 4 major active ingredient encapsulation techniques are known: manufacturing granulates in the presence of substrates, encapsulation techniques which implement β-cyclodextrines, silicone emulsions, and organic polymers.

The first category therefore pertains to processes for manufacturing granulates containing an agrochemical active ingredient, said ingredient being coated, milled together, or adsorbed onto a mineral or organic substrate, which is easily to spread. For example, the document JP 92 35203 describes a method for manufacturing a moistenable powder containing at least one agrochemical active ingredient fixed onto a diatomaceous earth-based, calcium carbonate-based, or cellulose-based substrate.

The second category is made up of encapsulation processes. They include processes which implement β-cyclodextrines which are natural "host" molecules obtained through the enzymatic degradation of starch. They appear in the form of cyclic oligomers of glucose and are characterized by the presence of the cavity which enables them to "accommodate a host molecule", so as to form an inclusion complex: using this mechanism, they can encapsulate agrochemical active ingredients, as described in the document FR 2,677,366. However, complexes based on β-cyclodextrines and an active ingredient must undergo an additional step of being coated by a protective material (a latex that will dry and solidify, in the example of the aforementioned document), so as to constitute a barrier enabling the gradual release of the active ingredient. Additionally, the stability of the inclusion complex that is formed primarily depends on the affinity of the cyclodextrine with the ingredient to be encapsulated: numerous active ingredients cannot be encapsulated by β-cyclodextrines.

A second method consists of encapsulating an agrochemical active ingredient by means of silicone emulsions in water: the high permeability of silicones enables them to slowly release the active ingredient molecules. In this manner, the document WO 2001/024631 describes the manufacturing of microcapsules used in agrochemistry via this method: they have a high mechanical resistance, which strengthens the protection of the active ingredient, and they enable a gradual release of the active ingredient, which leads to extended effectiveness. Such a method, however, relies on the solubility or compatibility of the active ingredient to be encapsulated with the silicone emulsion that is used, which does not make it possible to encapsulate all agrochemical active ingredients. Finally, there is a third category of encapsulation processes based on the use of organic polymers. They include coacervation methods, which rely on coating an emulsion of active ingredients with a precipitated polymer film. The precipitation is done using a colloidal polymer solution, which has voluntarily been destabilized. The precipitate, known as coacervate, will adsorb onto the droplets of the emulsion containing the molecules to be coated. To that end, the document U.S. Pat. No. 4,376,113 describes a method for encapsulating an active ingredient (insecticides, herbicides, biocides, fungicides, and acaricides are claimed) by coacervation and microencapsulation, by means of water-soluble hydroxyethylcellulose.

However, the coacervation processes require the prior manufacturing of an emulsion of active ingredients to be encapsulated, which constitutes an additional step beyond coacervation. Additionally, this technique does not enable the encapsulation of water-soluble active ingredients, because they cannot be placed in the emulsion. Furthermore, this method relies on the compatibility of the active ingredients with the polymers used for coacervation, which does not make it "universal".

Another encapsulation method based on the implementation of polymers is polycondensation. This method relies on the polycondensation of two monomers, one of them being compatible with the encapsulation medium, and the other being compatible with the substance to be encapsulated. This technique is described in the document "Microencapsulation of pesticides by interfacial polymerization utilizing isocyanate or aminoplast chemistry" (Pesticide Science, December 1998. vol. 54, n°4, pp. 394-400), which demonstrates how this succeeds at avoiding the oxidative degradation of pesticides, while controlling their evaporation kinetics. In parallel, the document EP 0,148,149 describes a method for encapsulating herbicide by interfacial polycondensation, the capsules formed being preferentially obtained by reaction between a diisocyanate and an amine. This method is therefore limited to active ingredients which do not chemically react with isocyanates: therefore, amines or acids which form major categories of molecules, particularly in fertilizers, cannot be encapsulated.

Thus, in order to resolve the multiple problems:
of encapsulating an agrochemical active ingredient, in order to effectively protect it from outside stresses, while protecting the person enlisted to handle it,
of slowing its release kinetics or spreading outside the capsule, in order to prevent overdosing the active ingredient or increasing the number of spreading operations,
of making it possible to formulate this active ingredient in the form of both a liquid or solid,
of providing a universal method for encapsulating any active ingredient, while meeting the aforementioned requirements and remedying the drawbacks of the prior art, The Applicant has developed an original manufacturing method, characterized in that it comprises the steps of:
a) mixing at least one HASE emulsion, at least one agrochemical active ingredient, at least one mineral or organic base, and water, said mixture having a pH greater than 5, preferentially 6, and very preferentially 7,
b) potentially precipitating the mixture obtained after step a) by adjusting the pH to a value less than 6, preferentially 3, in order to obtain a dispersion of solid particles in water,
c) potentially isolating the solid particles obtained after step b) by removing the water.

One of the originalities of the inventive method is using HASE emulsions, which have an associative hydrophobic monomer. This monomer has a property, when the emulsion is neutralized at a sufficiently high pH (>5), of creating associative interactions which strengthen the thickening effect, as compared to a polymer that does not have such monomers. These associative interactions between hydrophobic groups separate domains which act as solvation cages for an active ingredient. One of the Applicant's merits is having identified and used the phenomenon of water structure via a HASE emulsion, with a pH greater than 5: doing so naturally protects the active ingredient dissolved in that solution.

Such an implementation of HASE emulsions is, as far as we are currently aware, a new use of these objects, which were broadly described in applications for painting (see documents FR 2,693,203, FR 2,872,815, FR 2,633 930), the field of cosmetics (see the aforementioned document FR 2,872, 815), or the cement industry (see the as-yet-unpublished French patent application with the docket number FR 07 00086). Furthermore, these technical fields are very far from the one pertaining to the present invention, and the aforementioned documents give no disclosures or instructions which could guide the person skilled in the art towards the present invention.

Consequently, in a first variant which consists of only implementing step a) of the inventive method, a mixture is obtained in which the molecules of the active ingredient are trapped in the solvation cages. Thus, the speed at which the active ingredient is released through the solvation cages formed by the hydrophobic aggregates of fully or partially neutralized HASE emulsions is slowed.

In a second variant of the inventive method, one may also implement a step b) of acidifying the mixture obtained after step a). As already indicated, this results in a dispersion in water of solid particles of the HASE polymer and the active ingredients.

In a third variant, step b) may also be implemented, but in addition to a subsequent step c), which consists of isolating the solid particles obtained after step b) by removing the water. As in the previous case, the active ingredients are isolated and therefore protected, while being released more slowly.

Additionally, another advantage of the inventive method is delivering an active ingredient in a form which protects it and slows its release, this form potentially being threefold:
- that of a liquid, which is an aqueous solution, when the product is prepared by only carrying out the inventive method's step of mixing at a pH greater than 5,
- that of a liquid, which is a dispersion of solid particles in water, when the preparation of the product further implements the step of precipitation at a pH less than 5,
- that of a solid made up of solid particles of the active ingredient, which were trapped inside the polymer particles, when the inventive method's step of isolation has been implemented.

The Applicant notes that the unity of the invention is particularly ensured between these three forms of embodiments of the invention owing to the implementation, in each of these forms, of the combination of:
- at least one copolymer of (meth)acrylic acid, a monomer ester of these acids, and a hydrophobic monomer,
- and at least one agrochemical active ingredient.

Finally, another advantage of the invention is that it may be implemented in order to trap a very large number of agrochemical active ingredients. Finally, the person skilled in the art has access to a very vast library of associative monomers. He can easily draw upon it in order to wisely choose the monomer that will have the best possible affinity with the active ingredient to be trapped.

DESCRIPTION OF THE INVENTION

A first object of the invention is therefore a method for manufacturing a formulation containing an agrochemical active ingredient, and characterized in that it comprises the steps of:
a) mixing at least one HASE emulsion, at least one agrochemical active ingredient, at least one mineral or organic base, and water, said mixture having a pH greater than 5, preferentially 6, and very preferentially 7,
b) potentially precipitating the mixture obtained after step a) by adjusting the pH to a value less than 5, preferentially 3, in order to obtain a dispersion of solid particles in water,
c) potentially isolating the solid particles obtained after step b) by removing the water.

In a first variant, the inventive method only implements step a).

In a second variant, the inventive method implements step a) followed by step b).

In a third variant, the inventive method implements step a) then step b) then step c).

In practice, during step a), the components (the active ingredient, water, HASE emulsion, and the mineral or organic base) are added during agitation in a reactor; the order in which they are added will be chosen by the person skilled in the art, particularly based on the water-solubility of the active ingredient to be encapsulated. The quantity of the mineral or organic base is obviously adjusted so as to obtain a pH with a value greater than 5, preferentially 6, or very preferentially 7. The Applicant indicates that the implementation of said base may potentially be followed in step a) by adding an acid, so as to bring the pH back down (while keeping it at a value greater than 5). The person skilled in the art thereby regulates the rheology of his formulation and adapts it to its application (the thickening effect of the HASE polymers actually being influenced by the medium's pH), depending on how viscous he wants the product to be.

The inventive method is further characterized in that during step a), 0.1% to 20%, preferentially 0.1% to 10%, and very preferentially 0.1% to 5% by dry weight of a HASE emulsion, in relation to the total weight of the aqueous formulation obtained after step a), is implemented.

The inventive method is further characterized in that during step a), 0.1% to 20% by dry weight of a hydrophobic or hydrophilic agrochemical active ingredient, in relation to the total weight of the aqueous formulation obtained after step a), is implemented.

The inventive method is further characterized in that a strong or somewhat strong is implemented during step b). This addition of an acid is distinguished here by the potential addition of acid during step a):
- during step a), the potentially added acid makes it possible to regulate the viscosity of the formulation while keeping the pH above 5,
- during step b), the added acid makes it possible to precipitate HASE polymers at a pH value less than 5.

The inventive method is further characterized in that the HASE emulsion contains at least one copolymer of (meth)acrylic acid, a non-water-soluble monomer which is preferentially a (meth)acrylic ester chosen very preferentially from among ethyl acrylate, butyl acrylate, methyl methacrylate and mixtures thereof, and a monomer containing at least one hydrophobic group.

The inventive method is further characterized in that said monomer containing at least one hydrophobic group has the general formula (I):

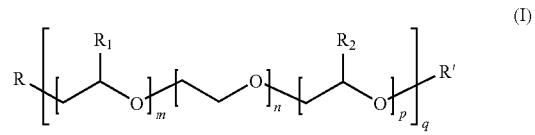

where:
- m, n, p and q are integers and m, n, p are less than 150,
- R has a polymerizable vinylic function,
- $R_1$ and $R_2$ are identical or different, and represent hydrogen atoms or alkyl groups,
- R' is a hydrophobic group comprising at least 6, preferentially at least 10, and very preferentially at least 12 carbon atoms.

The inventive method is further characterized in that the water is removed by evaporation or centrifugation during step c). However, the person skilled in the art may implement any other technique intended to remove the mixture's water achieved after step b). The method is finally characterized in that the agrochemical active ingredient is hydrophilic in a first variant. In a second variant, it is characterized in that the agrochemical active ingredient is hydrophobic.

A further object of the invention is the aqueous formulation containing at least one agrochemical active ingredient, and obtained by implementing step a) of the previously described method.

This aqueous formulation containing at least one agrochemical active ingredient is characterized:

1. in that it contains water, at least one HASE emulsion, at least one mineral or organic base, and at least one agrochemical active ingredient,
2. and in that it has a pH greater than 5, preferentially 6, and very preferentially 7.

This aqueous formulation is further characterized in that it contains 0.1% to 20%, preferentially 0.1% to 10%, and very preferentially 0.1% to 5% by dry weight of at least one HASE emulsion, in relation to its total weight.

This aqueous formulation is further characterized in that it contains 0.1% to 20%, by dry weight, of a hydrophilic or hydrophobic agrochemical active ingredient, in relation to its total weight.

This aqueous formulation is further characterized in that the HASE emulsion contains at least one copolymer of (meth)acrylic acid, a non-water-soluble monomer which is preferentially a (meth)acrylic ester chosen very preferentially from among ethyl acrylate, butyl acrylate, methyl methacrylate and mixtures thereof, and a monomer containing at least one hydrophobic group.

This aqueous formulation is further characterized in that said monomer containing at least one hydrophobic group has the general formula (I):

$$R\left[\left[\begin{array}{c}R_1\\ \phantom{x}\\ O\end{array}\right]_m\left[O\right]_n\left[\begin{array}{c}R_2\\ \phantom{x}\\ O\end{array}\right]_p\right]_q R'$$ (I)

where:
m, n, p and q are integers and m, n, p are less than 150,
R has a polymerizable vinylic function,
$R_1$ and $R_2$ are identical or different, and represent hydrogen atoms or alkyl groups,
R' is a hydrophobic group comprising at least 6, preferentially at least 10, and very preferentially at least 12 carbon atoms.

Another object of the invention resides in the formulation made up of solid particles dispersed in water, and obtained by implementing the step of precipitation b) of the method described above.

This dispersion of solid particles in water is characterized in that the solid particles that make it up contain an agrochemical active ingredient and a copolymer of (meth)acrylic acid, a non-water-soluble monomer which is preferentially a (meth)acrylic ester chosen very preferentially from among ethyl acrylate, butyl acrylate, methyl methacrylate and mixtures thereof, and a monomer containing at least one hydrophobic group.

This dispersion of solid particles in water is further characterized in that said monomer containing at least one hydrophobic group has the general formula (I):

$$R\left[\left[\begin{array}{c}R_1\\ \phantom{x}\\ O\end{array}\right]_m\left[O\right]_n\left[\begin{array}{c}R_2\\ \phantom{x}\\ O\end{array}\right]_p\right]_q R'$$ (I)

where:
m, n, p and q are integers and m, n, p are less than 150,
R has a polymerizable vinylic function,
$R_1$ and $R_2$ are identical or different, and represent hydrogen atoms or alkyl groups,
R' is a hydrophobic group comprising at least 6, preferentially at least 10, and very preferentially at least 12 carbon atoms.

A further object of the invention resides in the formulation made up of solid particles obtained by implementing the isolation step c) of the method described above.

These solid particles are characterized in that they contain at least one agrochemical active ingredient and at least one copolymer of (meth)acrylic acid, a non-water-soluble monomer which is preferentially a (meth)acrylic ester chosen very preferentially from among ethyl acrylate, butyl acrylate, methyl methacrylate and mixtures thereof, and a monomer containing at least one hydrophobic group.

These solid particles are also characterized in that said monomer containing at least one hydrophobic group has the general formula (I):

$$R\left[\left[\begin{array}{c}R_1\\ \phantom{x}\\ O\end{array}\right]_m\left[O\right]_n\left[\begin{array}{c}R_2\\ \phantom{x}\\ O\end{array}\right]_p\right]_q R'$$ (I)

where:
m, n, p and q are integers and m, n, p are less than 150,
R has a polymerizable vinylic function,
$R_1$ and $R_2$ are identical or different, and represent hydrogen atoms or alkyl groups,
R' is a hydrophobic group comprising at least 6, preferentially at least 10, and very preferentially at least 12 carbon atoms.

A final object of the invention is the use of aqueous formulations of at least one agrochemical active ingredient, aqueous dispersions of solid particles of at least one agrochemical active ingredient, and solid particles of at least one agrochemical active ingredient, as an agent with the triple function of protecting an agrochemical active ingredient from outside stresses, slowing its release, and protecting the people who handle it.

EXAMPLES

Example 1

This example illustrates the inventive method, which involves first creating in accordance with step a) an aqueous formulation of an agrochemical active ingredient that is Bordeaux mixture (a copper-based polyvalent fungicide), in the presence of a HASE emulsion, and at a pH greater than 5. The Bordeaux mixture is insoluble in water; its characteristic blue color will make it possible to tell whether it is encapsulated in the polymer particles or has been released into the water.

These formulations are then precipitated in accordance with step b) of the inventive method, by lowering the pH to a value less than 5: this shows how the Bordeaux mixture becomes trapped within the polymer particles.

Next, in accordance with step c), the previously obtained capsules are filtered so as to obtain solid particles of the polymer that encapsulated the Bordeaux mixture.

This example therefore illustrates the various objects of the invention.

Test No. 1
This test is a control.

6.99 g of Bordeaux mixture was placed in 353.01 g of bipermutated water. It is verified that the Bordeaux mixture is not soluble in water, and decants very quickly. This mixture is used today in this way, which raises the particular problem of a large quantity of active ingredients having decanted to the bottom of the container.

Test No. 2

This test illustrates the invention.

In accordance with step a) of the inventive method, first 1 liter 66.6 g of a HASE emulsion with 30% solids content sold by COATEX™ under the name DV540 is placed in a reactor. Next, 300 g of bipermutated water are added, followed by 7 g of powdered Bordeaux mixture.

Next, 50% sodium was added so as to set the pH to a value of 8.5.

This results in a viscous paste in which the active ingredient is trapped in solvation cages of the HASE polymer.

Next, 80 mL of a 4% solution of phosphoric acid were poured onto this paste (while being agitated). The pH is then equal to 6.1.

This results in a blue, liquid formulation which remains stable for three weeks.

In accordance with step b) of the inventive method, 175 grams of the previously obtained formulation are taken, and 50 mL of a 4% solution of phosphoric acid are added. This results in 225 grams of a formulation with a pH of 2.6, made up of polymer capsules which have a very deep blue color: this therefore means that the Bordeaux mixture is indeed encapsulated.

In accordance with step c) of the inventive method, the medium is then easily filtered in order to obtain the solid particles.

Example 2

This example illustrates the inventive method wherein, in accordance with step a) of the inventive method, an aqueous formulation of an agrochemical active ingredient which is cypermethrine (CAS number 52315-07-8) is created: This is an active phytosanitary product substance with an insecticidal effect, which belongs to the chemical family of synthetic pyrethrinoids.

Its solubility in water is equal to 0.01 mg/L.

Here, it is shown how the inventive method makes it possible to multiply the solids-content quantity of cypermethrine dissolved in the water by more than 3 million (the cypermethrine actually being trapped by the polymer's solvation cages).

Test No. 3

This test illustrates the invention.

0.82 grams of cypermethrine are placed in a 0.5 liter reactor, then 182 grams of bipermutated water, then 16.5 grams of a HASE emulsion with a solids content of 30%.

This emulsion is made up of, expressed as a percentage by weight of monomers in relation to the total weight of the monomers:
  38.2% methacrylic acid,
  26.3% methyl methacrylate and 26.3% ethyl acrylate,
  9.2% of a hydrophobic monomer with formula (I) wherein R is a methacrylate, $R_1$ and $R_2$ designate the methyl radical, m+n+p=25, q=1, and R' is a linear alkyl hydrophobic group having 20 carbon atoms.

In accordance with step a) of the method, the medium is neutralized by adding sodium until a pH equal to 8.6 is achieved.

This results in a viscous gel.

Next, 40 grams of a 4% solution of phosphoric acid are poured in order to achieve a pH equal to 5.2.

This results in a slightly cloudy solution: the cypermethrine has been trapped in the solvation pages created by the HASE polymer. Thus, 3.4% cypermethrine by weight has been trapped in the water, while the solubility of this product as-is extremely low (0.01 mg/L, i.e. 0.000001% by weight of the water-soluble material). The solubility of the cypermethrine has therefore been multiplied by more than 3 million.

Test No. 4

This test illustrates the invention.

0.82 grams of cypermethrine are placed in a 0.5 liter reactor, then 182 grams of bipermutated water, then 16.5 grams of a HASE emulsion with a solids content of 30%.

This emulsion is made up of, expressed as a percentage by weight of monomers in relation to the total weight of the monomers:
  38.0% methacrylic acid,
  53.0% ethyl acrylate,
  9.0% of a hydrophobic monomer with formula (I) wherein R is a methacrylate, $R_1$ and $R_2$ designate the methyl radical, m+n+p=25, q=1, and R' is a linear alkyl hydrophobic group having 16 carbon atoms.

In accordance with step a) of the method, the medium is neutralized by adding sodium until a pH equal to 8.5 is achieved.

This results in a viscous gel.

Next, 40 grams of a 4% solution of phosphoric acid are poured in order to achieve a pH equal to 5.1.

This results in a slightly cloudy solution: the cypermethrine has been trapped in the solvation pages created by the HASE polymer. Just as before, 3.4% cypermethrine by weight has been trapped in the water, multiplying its solubility by more than 3 million.

The invention claimed is:

1. A method for manufacturing a formulation comprising an agrochemical active ingredient, comprising:
  a) mixing at least one HASE (hydrophobically alkali swellable emulsion) emulsion, at least one agrochemical active ingredient, at least one mineral or organic base, and water, to produce a mixture having a pH greater than 5, and
  b) precipitating the mixture after said mixing by adjusting the pH to a value less than 6 in order to obtain a dispersion of solid particles in water.

2. The method according to claim 1, comprising precipitating the mixture obtained after said mixing by adjusting the pH to a value less than 3 in order to obtain a dispersion of solid particles in water.

3. The method according to claim 2, further comprising isolating the solid particles obtained after said precipitating by removing the water.

4. The method according to claim 1, wherein said mixture comprises 0.1% to 20%, by dry weight of a HASE emulsion, in relation to the total weight of the mixture.

5. The method according to claim 1, wherein said mixture comprises 0.1% to 20% by dry weight of a hydrophobic or hydrophilic agrochemical active ingredient, in relation to the total weight of the mixture.

6. The method according to claim 2, wherein a strong acid is implemented during said precipitating.

7. The method according to claim 1, wherein the HASE emulsion comprises at least one copolymer of (meth)acrylic acid, a non-water-soluble monomer and a monomer comprising at least one hydrophobic group.

8. The method according to claim 7, wherein said at least one hydrophobic group is represented by formula

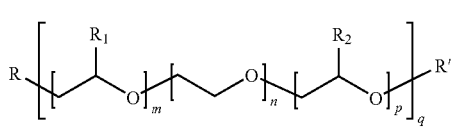
(I)

where:
m, n, p and q are integers and m, n, p are less than 150,
R has a polymerizable vinylic function,
$R_1$ and $R_2$ are identical or different, and represent hydrogen atoms or alkyl groups,
R' is a hydrophobic group comprising at least 6 carbon atoms.

9. The method according to claim 3, wherein the water is removed by evaporation or centrifugation during said isolating.

10. The method according to claim 1, wherein the agrochemical active ingredient is hydrophilic.

11. The method according to claim 1, wherein the agrochemical active ingredient is hydrophobic.

12. The method according to claim 7, wherein the non-water soluble monomer is a (meth) acrylic ester.

13. The method according to claim 12, wherein the (meth) acrylic ester is at last one selected from the group consisting of ethyl acrylate, butyl acrylate or methyl methacrylate.

14. The method according to claim 1, comprising:
a) mixing at least one HASE emulsion, at least one agrochemical active ingredient, at least one mineral or organic base, and water, to produce a mixture having a pH greater than 6.

15. The method according to claim 14, further comprising precipitating the mixture obtained after said mixing by adjusting the pH to a value less than 3 in order to obtain a dispersion of solid particles in water.

16. The method according to claim 1, comprising:
a) mixing at least one HASE emulsion, at least one agrochemical active ingredient, at least one mineral or organic base, and water, to produce a mixture having a pH greater than 7.

17. The method according to claim 16, further comprising precipitating the mixture obtained after said mixing by adjusting the pH to a value less than 3 in order to obtain a dispersion of solid particles in water.

18. The method according to claim 8, comprising:
a) mixing at least one HASE emulsion, at least one agrochemical active ingredient, at least one mineral or organic base, and water, to produce a mixture having a pH greater than 7, and
b) precipitating the mixture obtained after said mixing by adjusting the pH to a value less than 3 in order to obtain a dispersion of solid particles in water.

* * * * *